US00PP21560P2

(12) United States Plant Patent
Schuurbiers

(10) Patent No.: US PP21,560 P2
(45) Date of Patent: Dec. 7, 2010

(54) ***PHYSOCARPUS* PLANT NAMED 'GELESQ'**

(50) Latin Name: *Physocarpus opulifolius*
Varietal Denomination: Gelesq

(76) Inventor: Marinus Martinus Hendrikus Schuurbiers, Jodendijk 51, NL-7211 Eefde (NL)

( * ) Notice: Subject to any disclaimer, the term of this patent is extended or adjusted under 35 U.S.C. 154(b) by 157 days.

(21) Appl. No.: 12/322,455

(22) Filed: Feb. 3, 2009

(51) Int. Cl.
*A01H 5/00* (2006.01)

(52) U.S. Cl. ..... Plt./226

(58) Field of Classification Search ..... Plt./226
See application file for complete search history.

(56) References Cited

U.S. PATENT DOCUMENTS

PP11,211 P * 2/2000 Kordes et al. ..... Plt./226
PP14,821 P2 * 5/2004 Wood ..... Plt./226

* cited by examiner

*Primary Examiner*—Wendy C. Haas
(74) *Attorney, Agent, or Firm*—Penny J. Aguirre

(57) ABSTRACT

A new cultivar of *Physocarpus opulifolius*, 'Gelesq', characterized by its dwarf, compact and broadly spreading plant habit habit, its unique foliage with leaves that are dark gray to purple-black in color, its ability to be readily propagated by stem cuttings, and its hardiness to U.S.D.A. Zone 2.

1 Drawing Sheet

Genus/species: *Physocarpus opulifolius.*
Varietal denomination: 'Gelesq'.

BACKGROUND OF THE INVENTION

The present invention relates to a new and distinct cultivar of *Physocarpus opulifolius* and will be referred to hereafter by its cultivar name, 'Gelesq'. 'Gelesq' represents a new cultivar of *Physocarpus*, a deciduous shrub grown for landscape use.

The new *Physocarpus* arose from a breeding program conducted by the Inventor at his nursery in Eefde, The Netherlands. The objective of the breeding program was to develop new *Physocarpus* cultivars with a compact growth habit making them suitable for use as dwarf groundcovers.

The new *Physocarpus* originate from a controlled cross-pollination made by the Inventor in a field in his nursery in summer of 1995. The female parent was *Physocarpus opulifolius* 'Monlo' (U.S. Plant Pat. No. 11,211) and the male parent was *Physocarpus opulifolius* 'Dart's Gold' (Not patented). 'Gelesq' was selected as a single plant from a population of progeny derived from the cross-pollination in Eefde, The Netherlands in summer of 1997.

Asexual reproduction of the new cultivar was first accomplished by stem cuttings by the Inventor in the summer of 1998 in Eefde, The Netherlands. The characteristics of this cultivar have been determined to be stable and are reproduced true to type in successive generations.

SUMMARY OF THE INVENTION

The following traits have been repeatedly observed and represent the characteristics of the new *Physocarpus*. These attributes in combination distinguish 'Gelesq' as unique and distinct from all other cultivars of *Physocarpus* known to the Inventor.

1. 'Gelesq' exhibits leaves that are a dark gray to purple-black in color.

2. The plant habit of 'Gelesq' is dwarf and compact with a low, broadly spreading form.
3. 'Gelesq' is propagated readily from stem cutting and forms well-developed fibrous root systems.
4. 'Gelesq' is hardy to U.S.D.A. Zone 2.

'Gelesq' was selected as unique for its dwarf, compact, and low spreading growth habit as compared to the upright growth habit that is typical of *Physocarpus* cultivars as well as for its leaves that are dark grey to purple-black in color. 'Monlo', the female parent, differs from 'Gelesq' in having foliage that is lighter and more red-purple in color and in having a large, upright growth habit. Dart's Gold, the male parent, differs from 'Gelesq' in having foliage that is yellow to gold in color, and in also having has a large, upright growth habit.

BRIEF DESCRIPTION OF THE DRAWING

The accompanying photographs were taken in September of a three year-old plant of 'Gelesq' as grown outdoors in a 25-liter container under full sun in Eefde, The Netherlands and are representative of the new *Physocarpus.*

The photograph in FIG. 1 provides a side view of a typical plant of 'Gelesq'.

Figure 1:
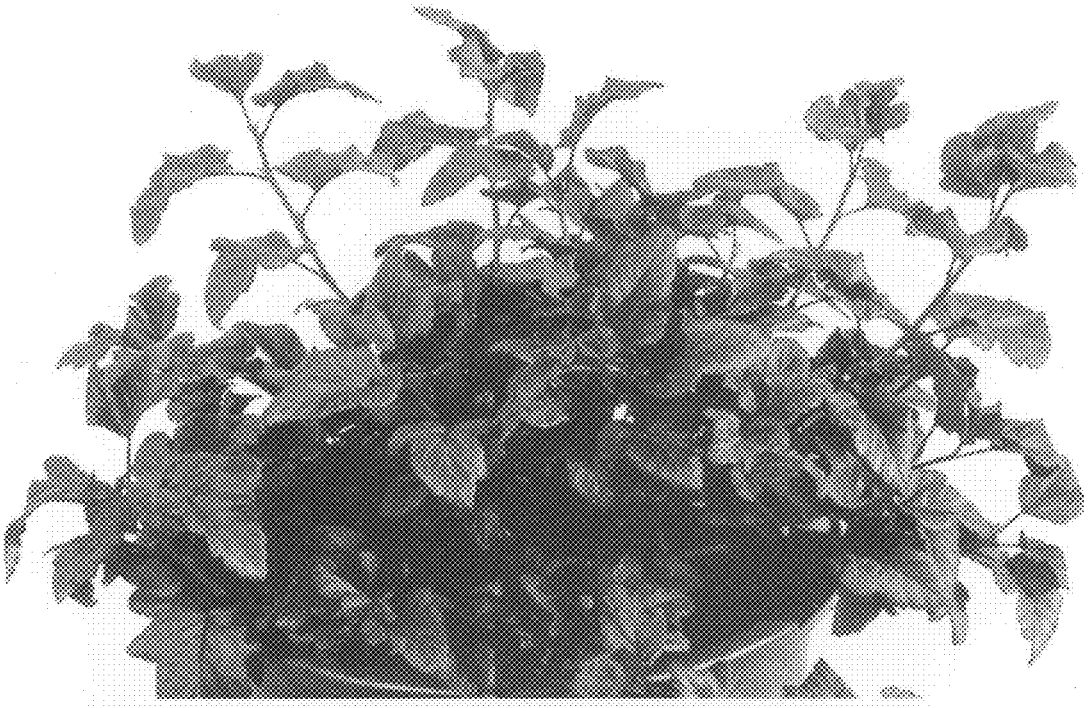
Figure 2:
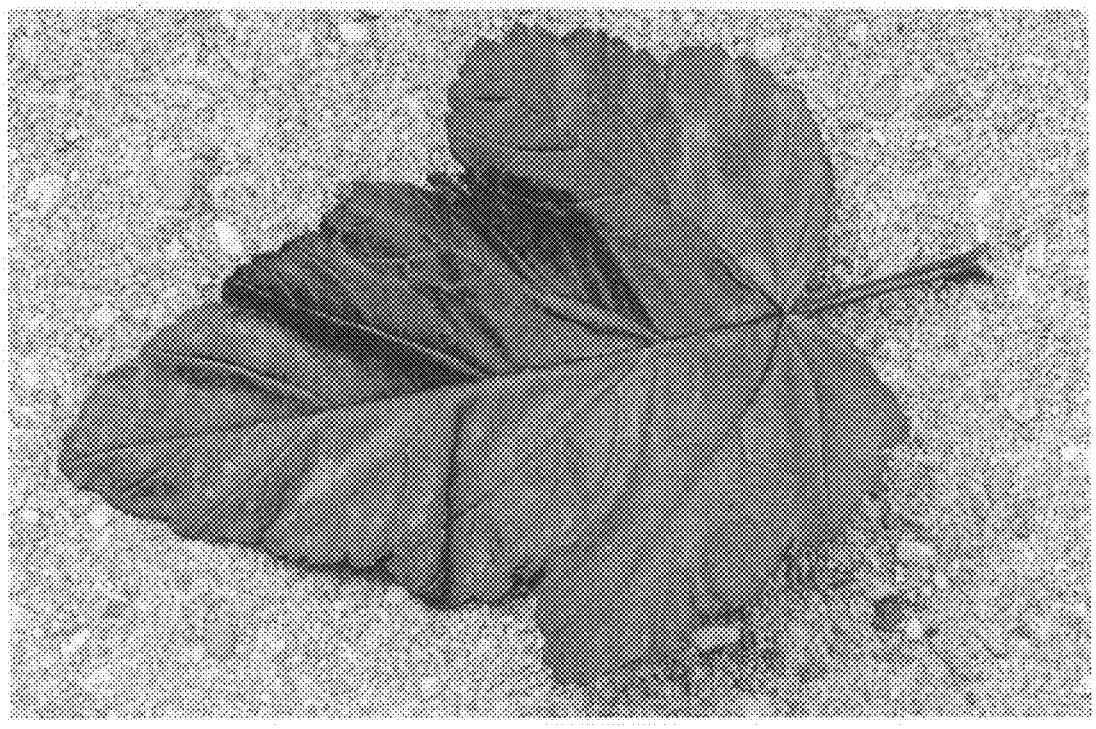

The photograph in FIG. 2 provides a close-up view of a single leaf of 'Gelesq'.

The colors in the photograph may differ slightly from the color values cited in the detailed botanical description, which accurately describe the colors of the new cultivar.

BOTANICAL DESCRIPTION OF THE PLANT

The following is a detailed description of a three year-old plant of the new cultivar as grown outdoors in a 25-liter container in Eefde, The Netherlands. Plants were grown under average day temperatures of 14° to 32° C. and average night temperatures of 5° to 15° C. Phenotypic differences may be observed with variations in environmental, climatic, and cultural conditions. The color determination is in accordance with The 2007 R.H.S. Colour Chart of The Royal Horticultural Society, London, England, except where general color terms of ordinary dictionary significance are used.

General description:

*Plant type.*—Deciduous shrub.

*Plant and growth habit.*—Dwarf, compact, broad-spreading.

*Blooming period.*—No flower observed to date.

*Height and spread.*—About 29 cm in height, about 69 cm in width.

*Hardiness.*—USDA Zone 2.

*Diseases and pest resistance.*—No particular susceptibility or resistance to diseases or pests has been observed.

*Root description.*—Fibrous, well-developed.

Growth and propagation:

*Growth rate.*—Slow to moderate.

*Propagation.*—Softwood stem cuttings.

Branch description:

*Branch color.*—New wood between N186C and 200A with underside 187A, mature bark 200B.

*Branch size.*—Lateral branches are an average of 3.5 mm in diameter and an average of 18.5 cm in length.

*Number of lateral branches.*—An average of 28 per plant.

*Branch surface.*—Glabrous, dull, bark on old, mature branches peels from the surface.

*Branch shape.*—Round, slightly ribbed lengthways.

*Branch internode length.*—Average 1.9 cm.

*Branch habit.*—Freely branching, removal of terminal tip (pinching) results in additional lateral branches.

*Branch strength.*—High.

Foliage description:

*Leaf shape.*—Ovate in outline, deeply tri-lobed, maple-like.

*Leaf division.*—Simple.

*Leaf base.*—Cordate.

*Leaf apex.*—Acute.

*Leaf venation.*—Palmate, color on upper surface between 147A and N186A, color on lower surface 147B and darkens to 187A to 187B near base of the leaf.

*Leaf margin.*—Tri-lobed, with secondary undulations, all edges are crenated, average of 3.5 teeth per cm.

*Leaf attachment.*—Petiolate.

*Leaf arrangement.*—Alternate.

*Leaf surface.*—Glabrous on upper and lower surfaces, very slightly rugose, glossy.

*Leaf length.*—Average of 8.1 cm.

*Leaf width.*—Average of 6.4 cm.

*Leaf number.*—About 7 per lateral branch.

*Leaf color.*—Young foliage; upper surface between N186A and 202A, lower surface near N187A, tinges of 189A, mature foliage; upper surface between N186 and 202A, lower surface 147B.

*Petiole size.*—About 2.1 cm in length, about 2 mm in width.

*Petiole shape.*—Sulcate.

*Petiole color.*—Upper surface between N186 and 202A, lower surface 187A to 187B.

*Petiole texture.*—Glabrous.

Flower description: No flowers observed in ten years of observation.

*Fruit and seed.*—None observed to date.

It is claimed:

1. A new and distinct cultivar of *Physocarpus* plant named 'Gelesq' substantially as herein illustrated and described.

* * * * *